US005733778A

United States Patent [19]

Matlashewski et al.

[11] Patent Number: 5,733,778

[45] Date of Patent: Mar. 31, 1998

[54] A2 GENE OF LEISHMANIA WHICH IS DIFFERENTIALLY-EXPRESSED IN AMASTIGOTE FORM

[76] Inventors: Gregory Matlashewski, 2571 Chestnut Cir., St-Lazare, Quebec, Canada, J0P 1V0; Hugues Chareat, 193p Sommet-Trinite, St-Bruno, Quebec, Canada, H3V 4P6

[21] Appl. No.: 452,531

[22] Filed: May 30, 1995

Related U.S. Application Data

[63] Continuation of Ser. No. 115,987, Sep. 3, 1993, abandoned.

[51] Int. Cl.$^6$ .......... C12N 15/63; C12N 15/12

[52] U.S. Cl. .......... 435/320.1; 435/69.3; 536/23.5

[58] Field of Search .......... 536/23.5; 435/69.3, 435/320.1

[56] References Cited

U.S. PATENT DOCUMENTS

| | | |
|---|---|---|
| 4,687,666 | 8/1987 | O'Daly . |
| 4,764,370 | 8/1988 | Fields et al. . |
| 4,801,530 | 1/1989 | Nogueira et al. . |
| 4,908,308 | 3/1990 | Van der Ploeg et al. . |
| 4,992,273 | 2/1991 | Monjour et al. . |
| 5,047,522 | 9/1991 | Nogueira et al. . |

OTHER PUBLICATIONS

Ellis et al. Mol. Biochem. Parasit 29:9–18 1988.

Brown et al. J. Biol. Med 4(6):365–76 1987.

Joshi et al. Mol. Biochem. Parasit. 58:345–354 1993.

WHO, Tropical Disease Report, 1989. 85–92.

Turco, S.J., and Descoteaux, A. 1992. The Lipophosphoglycan of *Leishmania* parasites. Annu. Rev. Microbiol. 46:65–94.

Sacks, D.L. 1989. Metacyclogenesis in *Leishmania* promastigotes. Exp. Parasitology. 69:100–103.

Sacks D.L., and da Silva, R.P. 1987. The generation of infective stage *L. major* promastigotes is associated with the cell–surface expression and release of a developmentally regulated glycolipid. J. Immunol. 139:3099–3106.

Sacks, D.L., Brodin T.N., Turco, S.J. 1990. Developmental modification of the lipophosphoglycan from *L. Major* promastigotes during metacyclogenesis. Mol. Biochemical Parasitol. 42:225–234.

Medina–Acosta, E., Karess, R.E., Schwartz H., and Russell, D.G. 1989. The promastigote surface protease (gp63) of *Leishmania* is expressed but differentially processed and localized in the amastigote stage. Mol. Biochemical Parasitol. 37:263–274.

Turco, S.J. and Sacks, D.L. 1991. Expression of stage–specific lipophosphoglycan in *Leishmania major* amastigotes. Mol. Biochemical Parasitol. 45:91–100.

McConville, M.J., and Blackwell J.M. 1991. Developmental changes in the glycosylated phosphatidylinositols of *L. donovani* J. Biol. Chem. 260:15170–15179.

Bogdan, C., Röllinghoff M., and Solbach, W. 1990. Evasion strategies of *Leishmania* parasites. Parasitol. Today. 6:183–187.

Modabber, F. 1989. Experiences with vaccines against cutaneous leishmaniasis: of men and mice. Parasitol. 98:S49–S60.

Joshi, M., Dwyer, D.M., and Nakhasi, H.L. 1993. Cloning and characterization of differentially expressed genes from in vitro–grown "amastigotes" of *Leishmania donovani*. Mol. Biochemical Parasitol. 58:345–354.

Descoteaux, A., and Matlashewski, G. 1989. *c–fos* and tumor necrosis factor gene expression in *Leishmania donovani*–infected macrophages. Mol.Cell. Biol. 9:5223–5227.

Doyle, P.S. Engel, J.C., Pimenta, P.F.P. da Silva, P. and Dwyer. 1991. *Leishmania donovani*: Long–term culture of axenic amastigotes at 37° C. Exp. Parasitol. 73:326–334.

Sambrook, J., Fristsch, E.F., and Maniatis. 1989. Molecular cloning. A laboratory guide. Cold Spring Harbor Laboratories Press, New York. pp. 7.26–7.29.

Sambrook, J., Fritsch, E.F., and Maniatis. 1989. Molecular cloning. A laboratory guide. Cold Spring Harbor Laboratories Press, New York. pp. 10.44–10.45.

Sambrook, J., Fritsch, E.F., and Maniatis. 1989. Molecular cloning. A laboratory guide. Cold Spring Harbor Laboratories Press, New York. pp. 9.38–9.40.

Sambrook, J., Fritsch, E.F., and Maniatis. 1989. Molecular cloning. A laboratory guide. Cold Spring Harbor Laboratories Press, New York. pp. 4.48.

Cruz,A., and Beverley, S.M. 1990. Gene–replacement in parasitic protozoa. Nature 348:171–173.

"Current Protocols in Molecular Biology", Ed. by F. M. Ausubel et al, vol. 1, Section IV.

Ellis et al, Mol. and Biochem. Parentology, 29 (1988) 9–18.

Jaffe et al, Infection and Immunity, vol. 57, No. 12, 1989.

Young and Davis, Proc. Natl. Acad. Sci., Vo. 80, pp. 1194–1198, 1983.

Gene 29 (1984) 251–254.

Brown et al, J. Biol. Med 4(6) 365–76 1987.

*Primary Examiner*—Anthony C. Caputa

[57] ABSTRACT

Differentially expressed Leishmania genes and proteins are described. One differentially expressed gene (A2) is expressed at significantly elevated levels (more than about 10 fold higher) in the amastigote stage of the life cycle when the Leishmania organism is present in macrophages than in the free promastigote stage. The A2 gene encodes a 22 kD protein (A2 protein) that is recognized by kala-azar convalescent serum and has amino acid sequence homology with an S-antigen of *Plasmodium falciparum* Vietnamese isolate VI. Differentially expressed Leishmania genes and proteins have utility as vaccines, diagnostic reagents, as tools for the generation of immunological reagents and the generation of attenuated variants of Leishmania.

5 Claims, 12 Drawing Sheets

FIG.8A.

```
                     XHO I
                     GAGCTCCCCCAGCGACCCTCTCGGCAACGCGAGCGCCCCAGTCCCCCCACGCACAACTTTGACCGAGCACA
    ORF II
    Met Lys Ile Arg Ser Val Arg Pro Leu Val Val Leu Leu Val Cys Val Ala Ala Val Leu Ala Leu
    ATG AAG ATC CGC AGC GTG CGT CCG CTT GTG GTG TTG CTG GTG TGC GTC GCG GCG GTG CTC GCA CTC

    Ser Ala Ser Ala Glu Pro His Lys Ala Ala Val Asp
 67 AGC GCC TCC GCT GAG CCG CAC AAG GCG GCC GTT GAC

                  Val Gly Pro Leu Ser Val Gly Pro
        103       GTC GGC CCG CTC TCC GTT GGC CCG

            Gln Ser Val Gly Pro Leu Ser Val Gly Pro
        127 CAG TCC GTC GGC CCG CTC TCT GTT GGC CCG

            Gln Ala Val Gly Pro Leu Ser Val Gly Pro
        157 CAG GCT GTT GGC CCG CTC TCC GTT GGC CCG

            Gln Ser Val Gly Pro Leu Ser Val Gly Pro
        187 CAG TCC GTC GGC CCG CTC TCT GTT GGC CCG

            Gln Ala Val Gly Pro Leu Ser Val Gly Pro
        217 CAG GCT GTT GGC CCG CTC TCC GTT GGC CCG

            Gln Ser Val Gly Pro Leu Ser Val Gly Pro Leu Ser Val Gly Pro
        247 CAG GCT GTT GGC CCG CTC TCC GTT GGC CCG CTC TCC GTT GGC CCG
```

FIG.8B.

```
    Gln Ser Val Gly Pro Leu Ser Val Gly Ser
292 CAG TCT GTC GGC CCG CTC TCC GTT GGC TCG

    Gln Ser Val Gly Pro Leu Ser Val Gly Pro
322 CAG TCC GTC GGC CCG CTC TCT GTT GGT CCG

    Gln Ser Val Gly Pro Leu Ser Val Gly Pro
352 CAG TCC GTC GGC CCG CTC TCT GTT GGC CCG

    Gln Ala Val Gly Pro Leu Ser Val Gly Pro
382 CAG GCT GTT GGC CCG CTC TCC GTT GGC CCG

    Gln Ser Val Gly Pro Leu Ser Val Gly Pro
412 CAG TCC GTC GGC CCG CTC TCT GTT GGC CCG

    Gln Ala Val Gly Pro Leu Ser Val Gly Pro
442 CAG GCT GTT GGC CCG CTC TCT GTT GGC CCG

    Gln Ser Val Gly Pro Leu Ser Val Gly Pro
472 CAG TCC GTT GGC CCG CTC TCC GTT GGC CCG

    Gln Ser Val Gly Pro Leu Ser Val Gly Ser
502 CAG TCT GTT GGC CCG CTC TCC GTT GGC TCG

    Gln Ser Val Gly Pro Leu Ser Val Gly Pro
532 CAG TCC GTC GGC CCG CTC TCT GTT GGT CCG

    Gln Ser Val Gly Pro Leu Ser Val Gly Pro
562 CAG TCC GTC GGC CCG CTC TCC GTT GGC CCG
```

FIG.8C.

```
    Gln Ser Val Gly Pro Leu Ser Val Gly Pro
592 CAG TCT GTC GGC CCG CTC TCC GTT GGC CCG

    Gln Ser Val Gly Pro Leu Ser Val Gly Pro
622 CAG TCC GTC GGC CCG CTC TCC GTT GGT CCG

    Gln Ser Val Gly Pro Leu Ser Val Gly Pro
652 CAG TCC GTT GGC CCG CTC TCC GTT GGC CCG

    Gln Ser Val
682 CAG TCC GTC

    Asp Val Ser Pro Val Ser ***
691 GAC GTT TCT CCG GTG TCT TAAGGCTCGGCGTCCGCTTTCCGGTGTGCGTAAAGTATATGCCATGAGGCATGGTGACGAGGCAAAC
776 CTTGTCAGCAATGTGGCATTATCGTACCCGTGCAAGAGCAACAGCAGAGCTGAGTGTTCAGGTGGCCACAGCACCACGCTCCTGTGACACT
867 CCGTGGGGTGTGTGTGACCTTGGCTGCTGTTGCCAGGCGGATGAACTGCGAGGGCCACAGCAGCGCAAGTGCCGCTTCCAACCTTGCGACT
958 TTCACGCCACAGACGCATAGCAGCGCCCTGCCTGTCGCGGCGCATGCGGGCAAGCCATCTAGA
                                                           XBA I
```

FIG.9.

```
                          10        20        30        40         50
A2                MKIRSVRPLVVLLVCVAAVLALSASAEPHKAAVDVGPLSVGPQSV-GPLSVG
                                             ::::::: :   : || |  ||::: || | |
Sant_P    PGSEGPKGTGGPGSEGPKGTGGPGSEGPKGTGGPGSEGPKGTGGPGSEGPKGTGGPGSEG
           100       120       130       140       150       160

                 60         70         80        90       100
A2         PQAV-GPLSVGPQSV-GPLSVGPQAV-GPLSVGPQSVGPLSVGPLSVGPQSV-GPLSVGS
           |::: || | ||::: || | ||::: || | ||:::|    || | ||::: || | |:
Sant_P     PKGTGGPGSEGPKGTGGPGSEGPKGTGGPGSEGPKGTG----GPGSEGPKGTGGPGSEGP
           170       180       190       200           210       220

                 60         70         80        90       100
A2         QSV-GPLSVGPQSV-GPLSVGPQAV-GPLSVGPQSV-GPLSVGPQAV-GPLSVGPQSV-G
           ::: || | ||::: || | ||::: || | ||::: || | ||::: || | ||::: |
Sant_P     KGTGGPGSEGPKGTGGPGSEGPKGTGGPGSEGPKGTGGPGSEGPKGTGGPGSEGPKGTGG
               230       240       250       260       270       280

                 60         70         80        90       100
A2         PLSVGPQSV-GPLSVGSQSV-GPLSVGPQSVGPLSVGSQSVGPLSVGSQSVGPLSVGSQS
           | | :|::: || | |:::: || | ||:::|| ::| :: :: : ||:::|  : :: :
Sant_P     PGSESPKGTGGPGSEGPKGTGGPGSEGPKGTGPKGTGGPGSEAGTEGPKGTGGPGSEAGT
               290       300       310       320       330       340

                 60         70         80        90       100
A2         VGPLSVGPQSVDVSPVS
            || ::|
Sant_P     EGPKGTGGPGSGGEHSHNKKKSKKSIMNMLIGV
               350       360       370
```

Southern blot analysis. Detection of L. donovani A2 amastigote-specific genes among other Leishmania species and subspecies.

A2 GENE OF LEISHMANIA WHICH IS DIFFERENTIALLY-EXPRESSED IN AMASTIGOTE FORM

This is a continuation of application Ser. No. 08/115,987 filed Sep. 3, 1993, now abandoned.

FIELD OF INVENTION

The present invention is related to molecular cloning of Leishmania genes and, in particular, to the cloning of amastigote differentially expressed genes from *Leishmania donovani.*

BACKGROUND TO THE INVENTION

Leishmania potozoans are the causative agents of human leishmaniasis, which includes a spectrum of diseases ranging from self-healing skin ulcers to fatal visceral infections. Human leishmaniasis is caused by at least thirteen different species and subspecies of parasites of the genus Leishmania. Leishmaniasis has been reported from about eighty countries and probably some 400,000 new cases occur each year. Recently, the World Health Organization has reported 12 million people to be infected (ref. 1—a listing of the references appears at the end of the disclosure).

*L. donovani* causes visceral leishmaniasis, also known as kala-azar. *L. brasiliensis* causes mucotaneous leishmaniasis and *L. major* causes cutaneous leishmaniasis. Untreated visceral leishmaniasis is usually fatal and mucocutaneous leishmaniasis produces mutilation by destruction of the naso-oropharyngeal cavity and, in some cases, death.

In addition, a major health problem has been created in areas of high infection when blood is collected for transfusion purposes. Since blood is a carrier of the parasites, blood from an infected individual may be unknowingly transferred to a healthy individual.

The Leishmania protozoans exist as extracellular flagellated promastigotes in the alimentary tract of the sandfly in the free-living state, and are transmitted to the mammalian host through the bite of the insect vector. Once introduced, the promastigotes are taken up by macrophages, rapidly differentiate into non-flagellated amastigotes and start to multiply within the phagolysosomal compartment. As the infected cells rupture, amastigotes subsequently infect other macrophages giving rise to the various symptoms associated with leishmaniasis (refs. 1 and 2). In this manner, it is the amastigote form of the parasite which is responsible for the pathology in humans.

While in the midgut of the insect, newly transformed promastigotes, functionally avirulent, progressively acquire capacity for infection and migrate to the mouthparts (ref. 3). This process, termed the metacyclogenesis, which occurs only in promastigotes, is concurrent with the differential expression of major surface glycoconjugates which mediate the migration of promastigotes in the alimentary tract and prepare the organism for the serum environment (refs. 4 and 5). In comparison, the promastigote to amastigote cytodifferentiation is a profound morphological and physiological transformation. During the promastigote to amastigote differentiation, the parasite looses its flagellum, rounds-up, changes its glycoconjugate coat (refs. 6, 7 and 8) and expresses a set of metabolic enzymes optimally active at low pH. The survival of the parasite inside the macrophage phagolysosome is associated with its ability to down-regulate many effector and accessory functions of its host cell, including oxygen metabolite-mediated killing and the capacity of the macrophage to act as an efficient antigen presenting cell (reviewed in, for example, ref. 9).

Leishmaniasis is, therefore, a serious disease and various types of vaccines against the disease have been developed, including live parasites; frozen promastigotes from culture; sonicated promastigotes; gamma-irradiated live promastigotes; and formalin-killed promastigotes treated with glucan (reviewed in, for example, ref. 10). However, none of these approaches have provided satisfactory results.

The promastigote-amastigote differentiation is important to the establishment of infection. It would be desirable to identify genes and gene products that are differentially expressed when the amastigotes are present in macrophages.

Joshi, et al. describe *L. donovani* genes that are expressed at about two-fold higher in in vitro generated and maintained "amastigotes" compared to promastigotes (ref. 11).

SUMMARY OF THE INVENTION

The present invention is directed towards the provision of a Leishmania protein that is differentially expressed in the amastigote stage when the Leishmania organism is present within macrophages and genes encoding the differentially expressed protein. The amastigote differentially expressed gene and protein are useful for the preparation of vaccines against disease caused by Leishmania, the diagnosis of infection by Leishmania and as tools for the generation of immunological reagents and the generation of attenuated variants of Leishmania.

In accordance with one aspect of the present invention, there is provided a purified and isolated DNA molecule, the molecule comprising at least a portion coding for a differentially expressed gene of a Leishmania organism, the differentially expressed gene being expressed at an increased level when the amastigote form of the Leishmania organism is present within a macrophage. The increased level of expression maybe at least about a ten-fold increase in expression. In one embodiment of the present invention, the differentially expressed gene may be a virulence gene of the Leishmania organism and may be required for maintenance of infection by the amastigote form of the Leishmania organism.

In a further aspect of the invention, the differentially expressed virulence gene is functionally disabled by, for example, deletion or mutagenesis, such as insertional mutagenesis, to produce an attenuated Leishmania organism for use as, for example, a live vaccine. Conveniently, strains of Leishmania from which differentially expressed genes may be isolated include *Leishmania donovani.*

Further aspects of the invention include the protein encoded by the differentially expressed gene, and the use of the protein in vaccination and diagnosis. Additional aspects of the invention include an attenuated strain of Leishmania in which the virulence gene is disabled and a vaccine comprising the same.

BRIEF DESCRIPTION OF THE DRAWINGS

FIG. 8A–C shows the nucleotide sequence (SEQ ID NO: 2) and deduced amino acid sequence (SEQ ID NO: 3) of the open reading frame II (ORF II) of the *Leishmania donovani* A2 gene as well as the nucleotide sequence (SEQ ID NO: 1) of the full length Xho I to Xba I fragment;

FIG. 9 shows the homology between the *Leishmania donovani* A2 protein (SEQ ID NO: 3) and the *Plasmodium falciparum* S antigen (SEQ ID NO: 4) within the repeated subunits of these proteins;

GENERAL DESCRIPTION OF THE INVENTION

Figure 1:
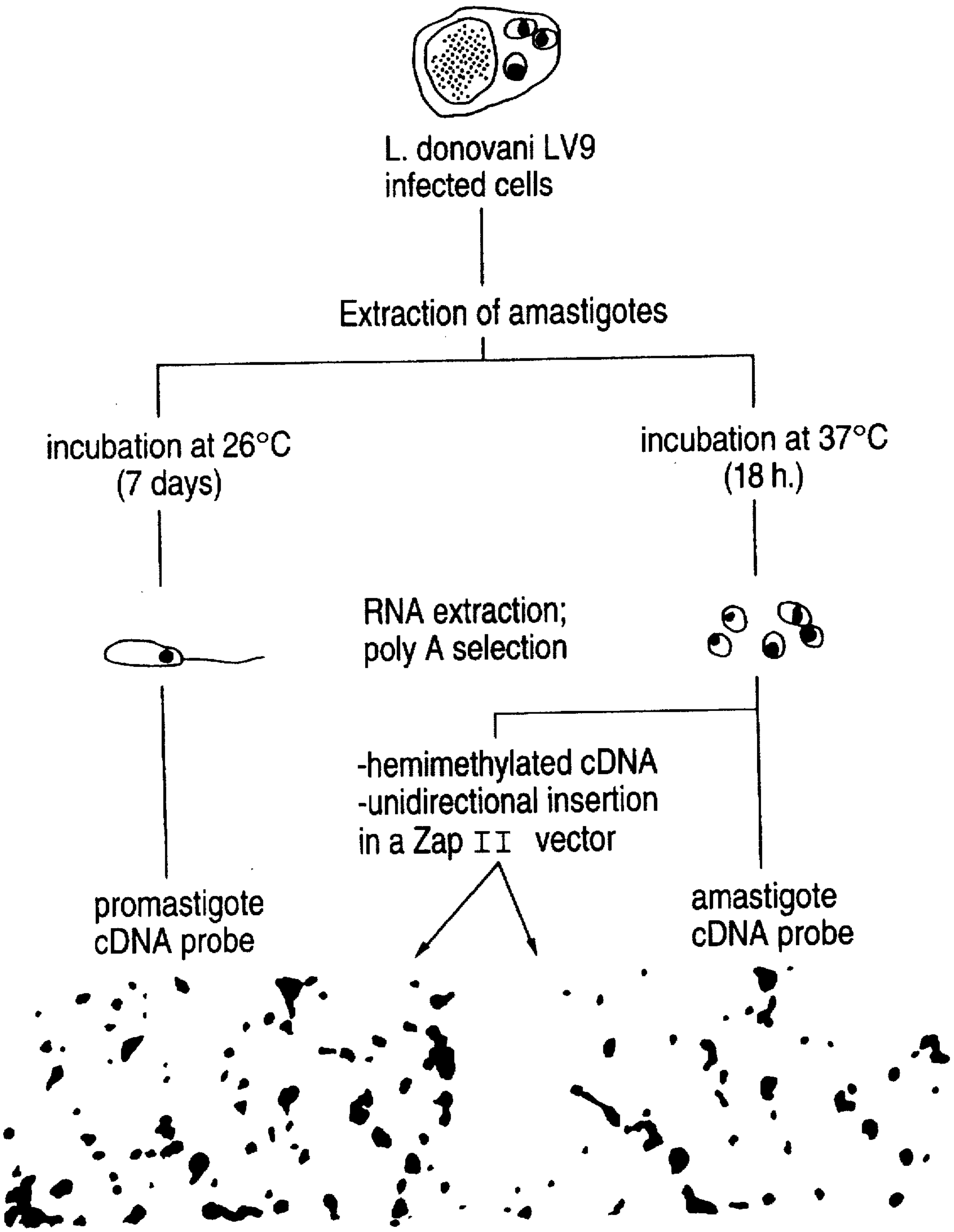
FIG. 1 shows a schematic outline of the amastigote cDNA library construction and differential screening with amastigote and promastigote-specific cDNA probes. An example of an amastigote-specific cDNA clone is indicated by an arrow on the colony hybridization autoradiogram.

Referring to FIG. 1, there is illustrated a method used for isolating a Leismania gene differentially expressed during the amastigote stage in the life cycle thereof. The method comprises the steps of (a) constructing a cDNA library from the Leishmania organism in the amastigote stage in the life cycle thereof; (b) constructing a first mixture of cDNA probes specific for the amastigote stage in the life cycle; (c) constructing a second mixture of cDNA probes specific for the promastigote stage in the life cycle; (d) separately probing the cDNA library with the amastigote and promastigote-specific cDNA probes in order to identify cDNA clones that are recognized by the amastigote mixture of cDNA probes but not the promastigote mixture of cDNA probes; and (e) isolating the cDNA clones identified in step (d).

The amastigote-specific cDNA clones identified by the above procedure can be further characterized by restriction enzyme analysis and their relatedness determined by Southern hybridization studies. To determine if cDNA clones identified by the above procedure represent amastigote-specific clones that are expressed at a higher level (more than about ten-fold higher) when the amastigote form of the Leishmania organism is present within macrophages, macrophages were infected with amastigotes and differentially-expressed gene transcripts were detected by Northern blot analysis. In an embodiment of the present invention, the differentially expressed Leishmania gene is *L. donovani* gene that is expressed at an increased level when the amastigote form of the Leishmania organism is present within a macrophage. The intracellular environment of the macrophage has an acidic pH of, for example, about 4.5. The differentially expressed genes include those having sequences, such as the DNA sequence set out in FIG. 8 (SEQ ID No: 2) or its complementary strand; and DNA sequences which hybridize under stringent conditions to such DNA sequences. Such differentially expressed gene sequences include the A2 gene of *L. donovani* having the DNA sequence set out in FIG. 8A–C and the invention includes a cDNA clone encoding the A2 gene depicted in FIG. 8A–C, which clone may be in the form of a plasmid, particularly that designated pGEC0 90 (FIG. 6), which has ATCC accession number ATCC 75510.

The differentially expressed genes may encode proteins, such as the 22 kD A2 protein (SEQ ID No: 3), being encoded by the longest open reading frame (ORF II) of the A2 gene. Most of the predicted A2 protein is composed of a repetitive sequence consisting of a stretch of ten amino acids repeated nineteen times (FIG. 8A–C). Since each unit of this repeat contains two serines, two valines, two leucines and two prolines separated from each other by five residues, the repeated region also may be considered as a stretch of five amino acids repeated thirty-eight times. The amino acid sequence of the A2 protein has homology with an S-antigen of *Plasmodium falciparum* (SEQ ID NO: 4), as shown in FIG. 9. As with the *L. donovani* A2 protein, the carboxy-terminal portion of the S-antigen of *P. falciparum* Vietnamese isolate VI is composed of a stretch of eleven amino acids repeated nineteen times; the repeated units of both proteins are 50% identical and 80% homologous.

Life cycle stage specific genes from Leishmania may be isolated in the present invention. Some of these genes are required for transition between the life cycle stages and include virulence genes of the Leishmania parasite, such as virulence genes that are required for maintenance of infection by the amastigote form of the Leishmania organism. These virulence genes may be functionally disabled by, for example, deletion or mutation, including insertional mutagenesis and, furthermore, the wild-type Leishmania gene may be replaced by the functionally disabled gene. The virulence genes may be functionally disabled by, for example, replacing the A2 gene by a selectable antibiotic resistance gene by homologous recombination following transformation of the Leishmania organism with a fragment of DNA containing the antibiotic resistance gene flanked by 5'- and 3'- non-coding DNA sequences. This process can be used to generate attenuated variants of Leishmania and the residual pathogenicity of the attenuated variants can be assessed in mice and hamsters pigs. It is likely that deletion of genes that are selectively expressed in the human host environment (that being when the Leishmania organism is inside the macrophage cell) result in an attenuated strain which cannot survive in humans but generates a protective immune response. Attenuated strains of Leishmania would be useful as live vaccines against the diseases caused by Leishmania and such attenuated strains form an aspect of the present invention.

Differentially expressed genes and proteins of Leishmania typified by the embodiments described herein are advantageous as:

- antigens for vaccination against the diseases caused by Leishmania.
- diagnostic reagents including hybridization probes, antigens and the means for producing specific antisera for (for example) detecting infection by Leishmania.
- target genes for functional disablement for the generation of attenuated Leishmania variants.

Vaccines comprising an effective amount of the protein encoded by the differentially expressed genes or of an attenuated strain of Leishmania and a physiologically-acceptable carrier therefor may utilize an adjuvant as the carrier and the protein may be presented to the immune system of the host in combination with an ISCOM or liposome. The vaccine may be formulated to be administered to a host in an injectable form, intranasally or orally, to immunize the host against disease.

BIOLOGICAL DEPOSITS

Figure 6:
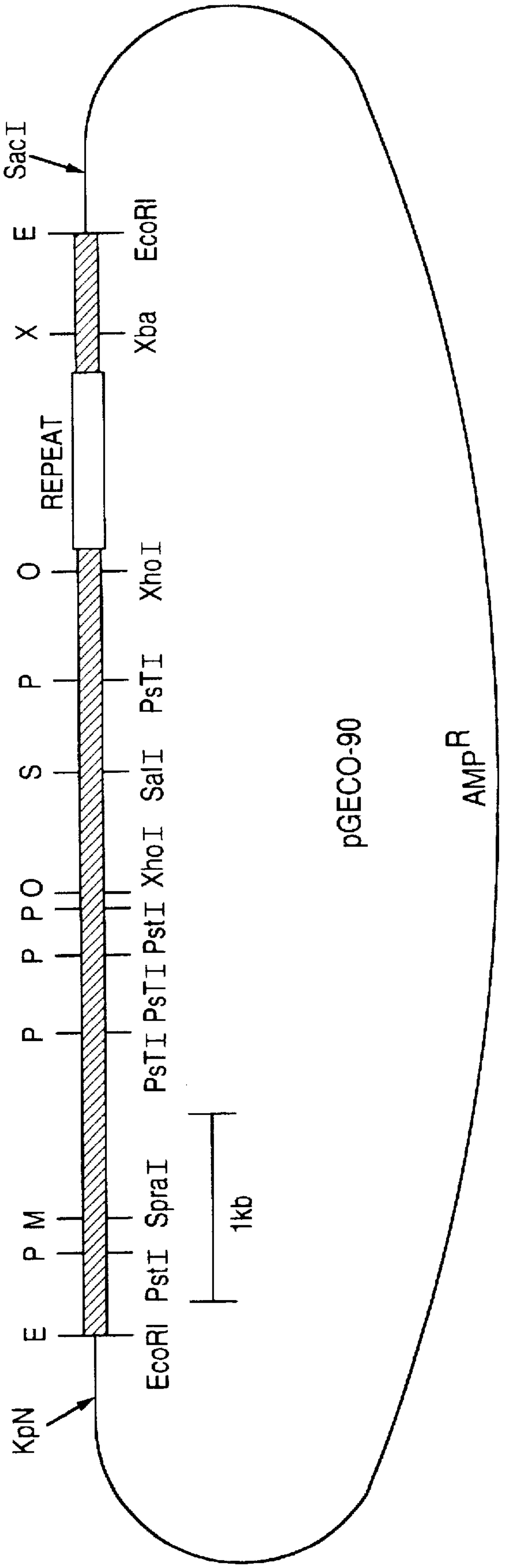
FIG. 6 shows a restriction map of plasmid pGECO 90 that contains the *L. donovani* A2 gene.

A plasmid pGECO 90 described and referred to herein was deposited with the American Type Culture Collection (ATCC) located at 12301 Parklawn Drive, Rockville, Md., 20852, USA, pursuant to the Budapest Treaty on Jul. 28, 1993 and prior to the filing of this application and assigned the ATCC accession number 75510. A diagram of this plasmid is shown in FIG. 6. The plasmid contains the A2 gene of *L. donovani* described herein. The plasmid will become available to the public upon grant of a patent based upon this United States patent application. The invention described and claimed herein is not to be limited in scope by the material deposited, since the deposited embodiment is intended only as an illustration of the invention. Any equivalent materials are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics and protein biochemistry used but not explicitly described in this disclosure and these Examples, are amply reported in the scientific literature and are well within the ability of those skilled in the art.

Example 1

This Example describes culturing and isolation of Leishmania organisms.

Amastigotes of the *L. donovani* Ethiopian LV9 strain were harvested from spleens of infected female gold Symian hamsters and purified as described previously (ref. 12). Briefly, parasites were released from tissue using an homogenizer, the mixture was centrifuged three times at 100 xg to remove cellular debris, and amastigotes were pelleted at 1500 xg. The pellet was resuspended in 0.17M sodium acetate to lyse contaminating red blood cells and amastigotes were recovered by centrifugation at 1500 xg. Organisms were incubated at 37° C. in complete RPMI medium (RPMI 1640 supplemented with 10% endotoxin free heat-inactivated FBS, 10 ml of 1M HEPES pH 7.3, 100 U of penicillin and 100 U of streptomycin per ml) for 18 hours prior to RNA extraction. After this period of incubation and multiple washes, the amastigote preparation was still physiologically active and relatively free of host cell contamination. To obtain promastigotes, LV9 strain amastigotes were allowed to differentiate in complete RPMI medium at 26° C., and cultured for at least seven days in the same medium before use (ref. 12).

Promastigotes of the *L. donovani* Sudanese strain 1S2D were cultivated and passaged in complete RPMI medium at 26° C. Amastigote-like organisms of the 1S2D strain were cultivated as described by Doyle et al. (ref. 13). The Sudanese strains 1S2D and 1S2D (wt) were obtained from Dr. S. Turco, the University of Kentucky, USA. The 1S2D (wt) promastigotes were adapted to grow in axenic conditions and had lost the ability to transform into infective promastigotes.

Example 2

This Example describes the preparation of and screening of a Leishmania cDNA library.

A method for isolating a Leishmania gene differentially expressed during the amastigote stage in the life cycle of the organism is illustrated in FIG. 1.

Total RNA of amastigotes and promastigotes was prepared by the guanidinium isothiocyanate method using RNAzol (Trademark of Cinna/biotecx Laboratories International Inc., Friendswood, Tex. for an enzyme inactivator); poly $A^+$ RNA was selected by oligo dT cellulose chromatography (grade 7:Pharmacia) as described by Sambrook et al. (ref. 14). A total of 10 μg of amastigote mRNA was used to construct an Eco RI/ Xho I unidirectional cDNA library of $10^6$ clones in the λ ZAP II phage vector (Trademark of Stratagene); hemi-methylated cDNA was produced using the manufacturers reagents and protocols. About 40,000 amastigote and promastigote-specific clones of the primary library were screened differentially with amastigote and promastigote stage-specific gene probes. The cDNA probes were prepared using oligo $dT_{12-18}$ primer (Pharmacia) and M-MLV reverse transciptase (BRL) following protocols previously described (ref. 15). Duplicate filters were hybridized with each probe for 18 h at 42° C. in 50% formamide, 6X SSC, 5X Denhardt's solution, 5% dextran sulfate. Membranes then were washed twice at room temperature in 1X SSC for 20 min, twice at 55° C. in 1X SSC, 0.1% SDS and then autoradiographed on X-OMAT (Trademark of Kodak) films with an intensifying screen for 18 to 72 hours. Areas on the plates containing putative clones of interest were picked and the phage pools were submitted to a second round of screening. An example of an amastigote-specific cDNA clone is indicated by the arrow on the plaque hybridization autoradiogram of FIG. 1.

Although cDNA clones representing promastigote-specific transcripts were more abundant than clones representing amastigote-specific transcripts, seven independent cDNA clones which only hybridized with amastigote-specific probes were isolated and termed 2, 3, 5, 6, 8, 9, 11. For each cDNA clone isolated, a Bluescript plasmid derivative was excised from the λZAP II recombinant phages in vivo using the helper phage R-408.

Example 3

This Example describes the characterization of amastigote-specific cDNA clones.

Figure 2:
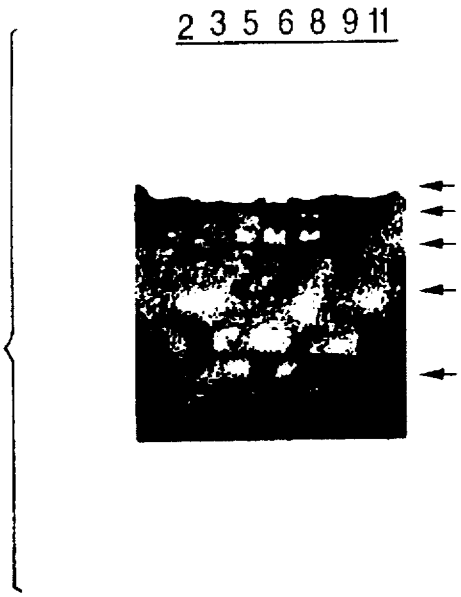
FIG. 2 shows a restriction enzyme and size analysis of *Leishmania donovani* amastigote-specific cDNA clones.
Figure 3:
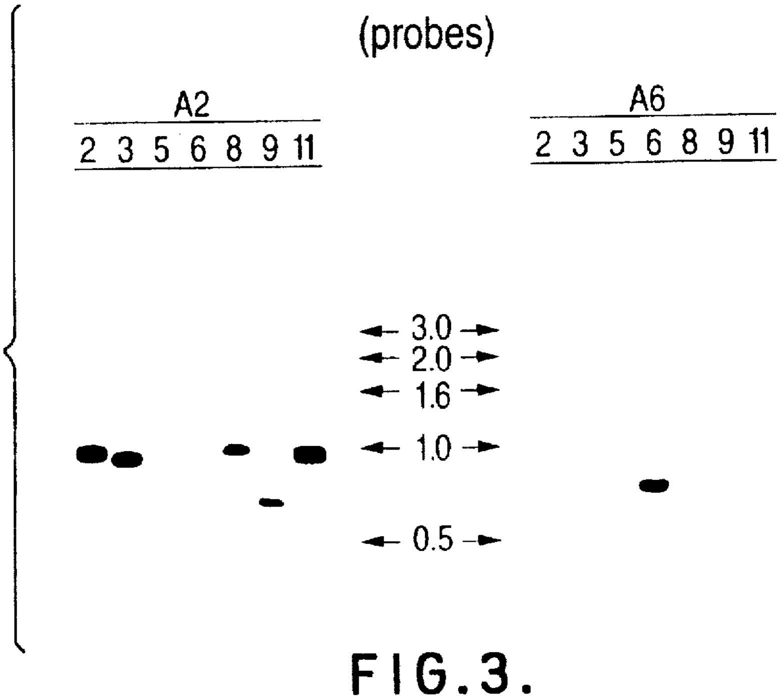
FIG. 3 shows a Southern blot analysis of *Leishmania donovani* amastigote-specific cDNA clones.

The insert size, of each of the Bluescript plasmids corresponding to the amastigote-specific cDNA clones was determined by restriction enzyme digestion and agarose gel electrophoresis (FIG. 2). Recombinant plasmids (A2, A3, A5, A6, A8, A9 and A11) were digested with Eco RI and Xho I to excise the cDNA inserts. Fragments were separated on a 1% agarose gel and stained with ethidium bromide. The cDNA inserts varied from 0.5 kb (A5) to 1.8 kb and A8 contained an internal Eco RI site. To determine if the amastigote-specific cDNA clones contain common sequences, Southern blot hybridization analysis of the Bluescript plasmids corresponding to the amastigote-specific cDNA clones was performed using clone A2 and clone A6 specific probes (FIG. 3).

For Southern blot analysis, 10 μg of total DNA was cut to completion with the restriction enzymes Eco RI and Xho I and separated on a 1% agarose gel. The restriction fragments were transferred to nylon membranes using standard procedures (ref. 16) and duplicates hybridized with α-$^{32}$P dCTP nick-translated probes representing the inserts of the cDNA clones A2 (0.9 kb) or A6 (0.6 kb). The A2 probe recognized five cDNAs (A2, A3, A8, A9 and A11) and the A6 cDNA only hybridized to itself. Thus, this Southern blot analysis indicated that cDNA clones A2, A3, A8, A9 and A11 contained homologous sequences but A5 and A6 were clones of unrelated amastigote-specific transcripts.

Figure 4:
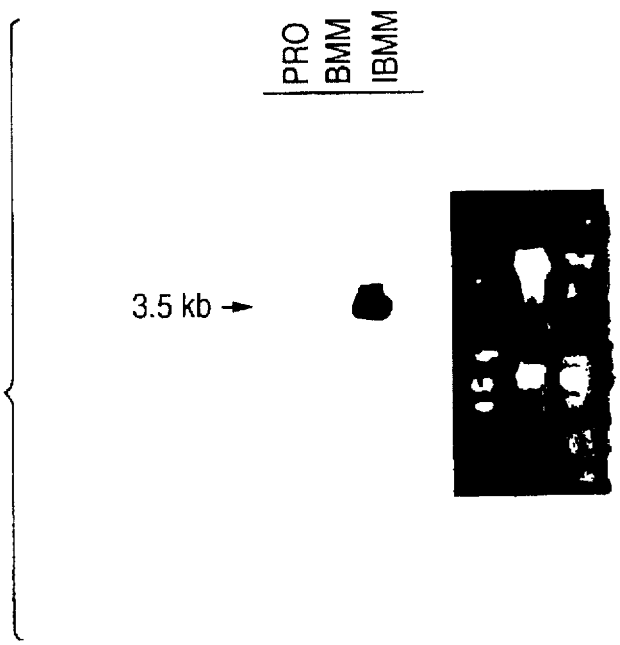
FIG. 4 shows a Northern blot analysis to demonstrate that A2-specific transcripts are present in amastigote-infected macrophages but not promastigotes.

To confirm that the A2 series of clones represented Leishmania genes that were differentially expressed when the Leishmania organism is present in macrophages compared to expression in the free-living promastigotes, Northern blot analysis was performed. Total RNA was extracted from bone marrow-derived macrophages (BMM), *L. donovani* LV9-infected BMM (IBMM) and *L. donovani* LV9 promastigotes (PRO). Murine bone marrow-derived macrophage cultures and *L. donovani* amastigote in vitro infections were carried out as previously described (ref. 12). The RNA species (15 μg) were separated on an agarose gel and stained with ethidium bromide prior to transfer (FIG. 4, right panel). The RNA was denatured by glyoxal treatment and transferred to a nylon membrane. The Northern blot was hybridized with labelled cDNA A2 (0.9 kb) fragment, as previously described (ref. 12) (FIG. 4, left panel). This probe recognized predominantly a 3.5 kb transcript present in amastigote-infected macrophages but not in promastigotes or in non-infected macrophages. This analysis showed that the A2 gene was differentially expressed at an increased level in amastigotes when they were present in macrophages compared to a free-living existence and that the increased expression was at least a ten fold increase.

Example 4

This Example describes the genomic arrangement and sequencing of the *Leishmania donovani* amastigote-specific A2 gene.

Figure 5:
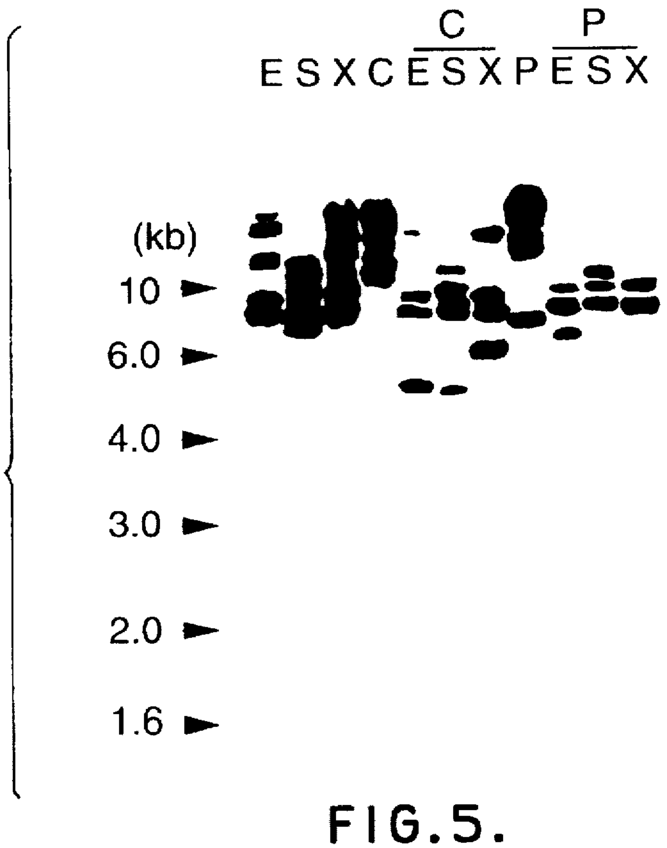
FIG. 5 shows a Southern blot analysis to demonstrate that A2 transcripts are encoded by a multigene family.

Regulation of transcription is one of the unusual features of the genetics of trypanosomatids. Copies of a gene or related genes are often clustered in tandem arrays on the same chromosome and a unique promoter region regulates expression of the cluster. Transcription leads to the synthesis of a polycistronic RNA molecule which is cleaved into monomeric units by trans-splicing prior to translation. The genomic arrangement of A2 related gene(s) was investigated by Southern blot analysis to determine whether it represents a multigene family. Total DNA was digested to completion with several restriction enzymes (E: Eco RI, S: SalI, X: Xba I, C: Cla I, P: pvu II). For double digests, the DNA was first cut to completion with Cla I or PvuII, the DNA precipitated and resuspended in the appropriate buffer for the second digestion. Restriction fragments were separated on a 0.7% agarose gel, transferred to a nylon membrane and hybridized with a 0.5 kb Pst I/Xho I fragment of the A2 cDNA insert nick-translated with $\alpha$-$^{32}$P dCTP. For each digest, the hybridization pattern displayed a series of bands of different intensities, clearly showing that many copies of the gene were present in the genome (FIG. 5). Moreover, common bands at about 6 to 8 kb for the Eco RI, Xba I and Sal I digests suggested an arrangement in tandem arrays. However, the presence of at least two other bands in each lane suggested that more than one cluster existed, each cluster being flanked by restriction fragments of different sizes. Alternatively, clusters also may carry copies of unrelated genes or intergenic regions of variable sizes.

To identify the protein coding region of A2, genomic clones carrying the A2 gene sequence were isolated. A partial genomic library containing 6 to 10 kb Eco RI fragments was constructed in the lambda ZAP II vector (Stratagene). More than 2,000 clones were screened on duplicate filters with probes prepared with the A2 cDNA using techniques and hybridization conditions described in Example 2. Eight clones were isolated and purified. Bluescript plasmid derivatives were excised from recombinant λ phages as for cDNA clones.

Figure 7:
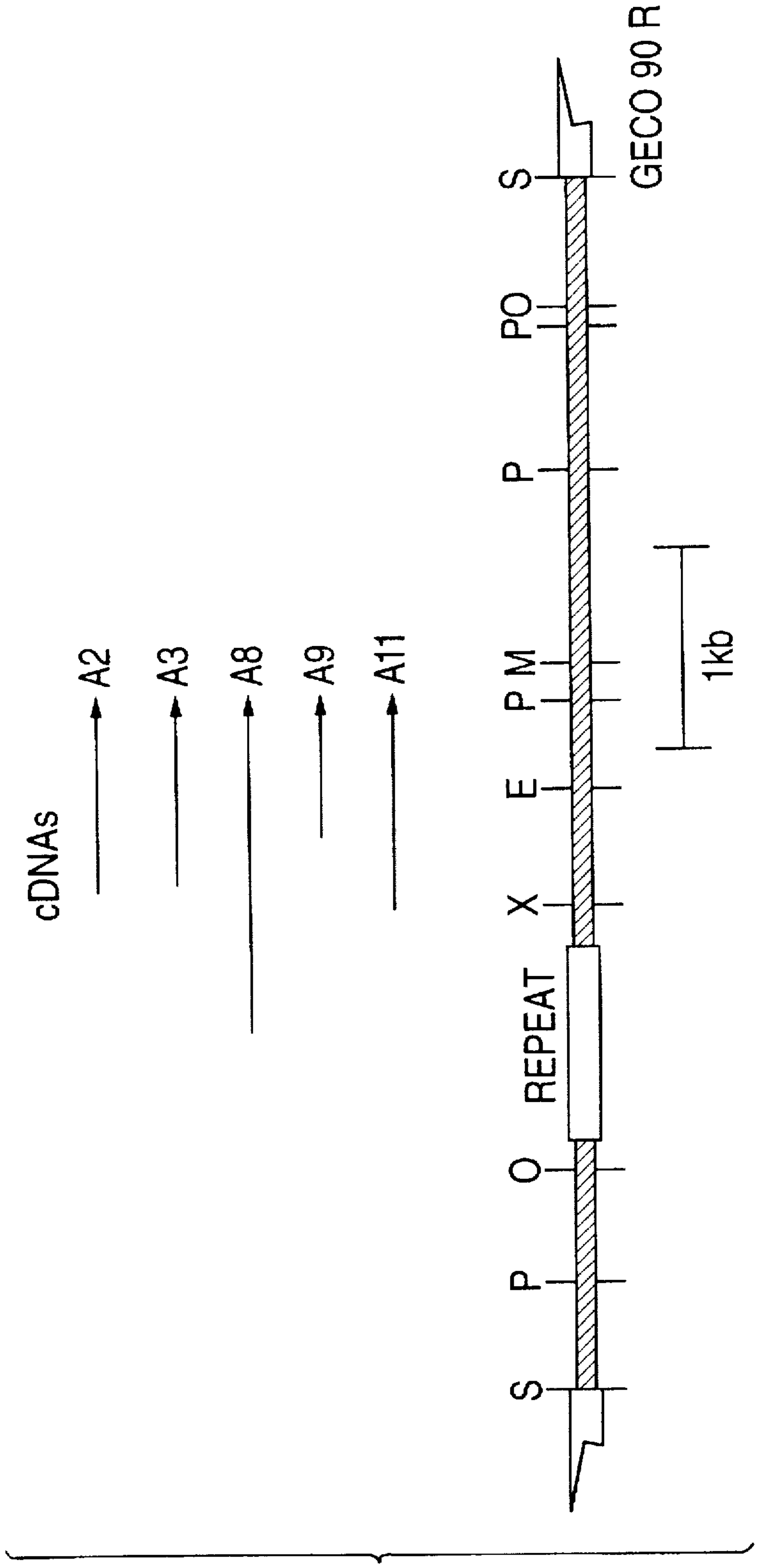
FIG. 7 shows a restriction map of a genomic clone of the A2 gene and its relationship to A2-related cDNAs.

The 1.9 kb Xho I/ Eco RI insert fragment of the A2 Bluescript clone was subcloned into the Bluescript phagemids KS$^+$ and KS$^-$ for sequencing. Nested deletions were carried out on both plasmids using Exo III exonuclease and S1 nuclease. Sequencing reactions were performed on single-strand DNA templates using the M13K07 helper phage according to published procedures (ref. 17) with the Deaza G/A sequencing mixes (Pharmacia) and d$^{35}$ATP or d$^{35}$CTP radio-isotopes. Reactions were analysed on 6% denaturing gels. The inserts of the genomic clones were mapped with several restriction enzymes and displayed similar patterns, except some inserts were longer than others. One of these clones, pGECO 90 (as shown in FIG. 6), was selected for further characterization. FIG. 7 shows the restriction map of the insert of pGECO 90 and how it corresponds to the A2 related cDNAs. The restriction enzymes shown in FIG. 7 are S: Sal I, P: Pst I, O: Xho I, X: Xba I, E: Eco RI, M: Sma I. Plasmid pGECO 90 contained unique sites for Sal I and Xba I, but no Cla I site, and this was consistent with the Southern blot analysis shown in FIG. 5. The DNA sequence flanking the Eco RI site on this genomic clone was determined and shown to correspond exactly to the related portion of the A8 cDNA, confirming that this fragment represented one unit of the tandem array.

The DNA sequence of the 1.9 kb Xho I/ Eco RI fragment of the pGECO 90 genomic clone corresponding to the 3.5 kb A2 transcript was determined (FIG. 8A–C) and compared to the cDNA's sequences. The longest open reading frame (ORF II) found was contained in the Xho I/Xba I 1.1 kb fragment and potentially encoded a 22 kD protein product (A2 protein). Stop codons were observed in two other frames and upstream from the initiating ATG. Most of this predicted A2 protein was composed of a repetitive sequence consisting of a stretch of ten amino acids repeated nineteen times. Since each unit of this repeat contains two serines, two valines, two leucines and two prolines separated from each other by five residues, the repeated region could also be considered as a stretch of five amino acids repeated thirty-eight times. The only hydrophobic domain was located at the amino terminal portion and may correspond to a signal peptide. The predicted amino acid sequence was compared with proteins reported in the Swiss-Prot database version using a Fasta algorithm (Canada Institute for Scientific and Technical Information: Scientific Numeric Database Service). The most striking identity was observed with an S-antigen of *Plasmodium falciparum* Vietnamese isolate VI. The alignment of the A2 protein sequence (A2) with the amino-terminal portion of the S-antigen of *P. falciparum* isolate VI is shown in FIG. 9. Identical residues are indicated by dashes and homologous amino acids by dots. As with the *L. donovani* A2 protein, the carboxy-terminal portion of this antigen of *P. falciparum* Vietnamese isolate IV is composed of a stretch of eleven amino acids repeated nineteen times. The repeated units of both proteins are 50% identical and 80% homologous. The S-antigen, as the CS-antigens of Plasmodium, are proteins which are stage-specific, being expressed in the mammalian host but not in the insect host. Therefore, the A2 and S-antigen genes from unrelated human infectious protozoa are expressed specifically in the mammalian host and encode similar proteins. Thus, the A2 and S-antigen proteins may perform similar functions and may be required to enable these protozoa to survive in humans and functional disablement of the A2 sequences in *L. donovani* may be expected to result in a non-infective promastigote useful as a live attenuated vaccine for leishmaniasis.

Example 5

This Example describes the functional disablement of differentially expressed genes in Leishmania.

One approach for the development of attenuated strains of Leishmania is to functionally disable amastigote-specific genes (such as the A2 gene) from the Leishmania genome (by for example deletion) using homologous recombination. Deletion of genes from protozoa (such as Leishmania) has been described (ref. 18). This procedure involves cloning DNA fragments 5'- and 3'- to the A2 gene and constructing a plasmid vector that contains these flanking DNA sequences sandwiching a neomycin resistance gene. This 5'-neo 3'- fragment of DNA then is used to transform *L. donovani* promastigotes to G418 resistance. *L. donovani* is diploid and deletion one allele of the A2 gene in such G418 resistant strains can be determined by Southern blot hybridization using A2 specific probes. The second A2 allele then can be deleted by constructing a second deleting vector containing the 5'- and 3'- A2 flanking sequences sandwiching a hygromycin resistance gene. Following transformation colonies are selected on medium containing G418 and hygromycin. Deletion of both copies of the A2 gene can be confirmed by Southern blot hybridization.

Example 6

This Example describes the expression of the *L. donovani* amastigote-specific A2 gene and the recognition of the A2 gene product by kala-azar immune sera.

Figure 10:
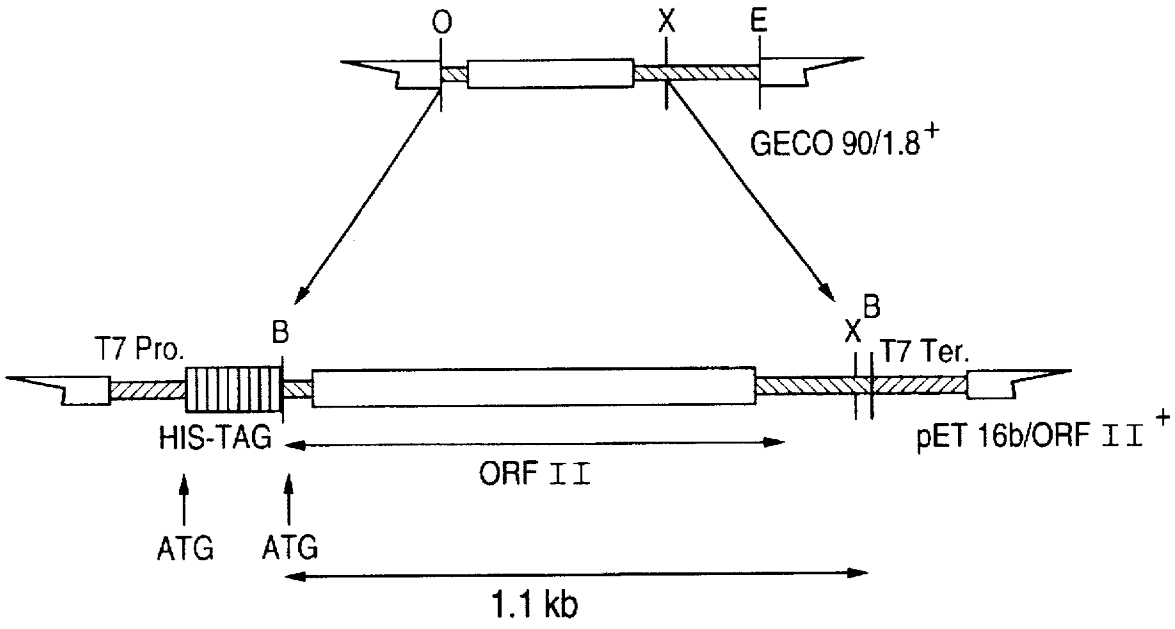
FIG. 10 shows the construction of a plasmid pET 16b/ORF II$^+$ for expression of the A2 protein.
Figure 11:
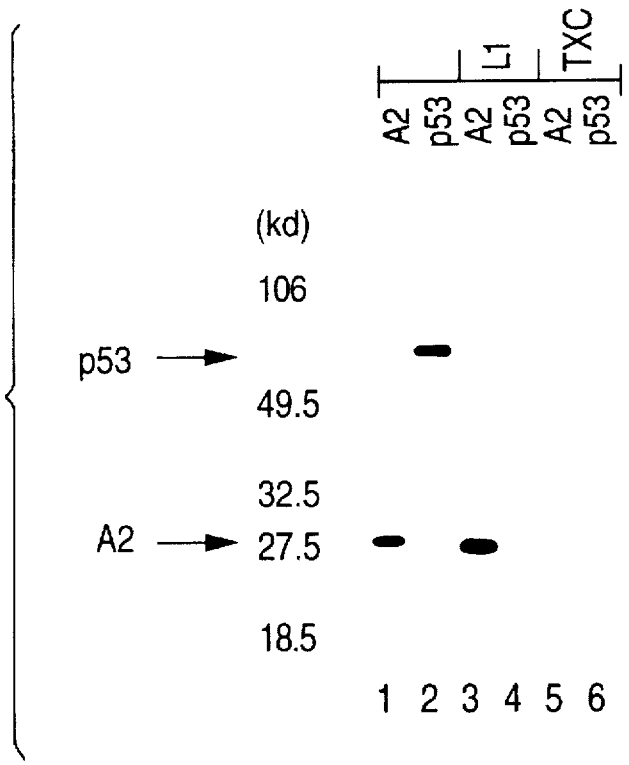
FIG. 11 shows the presence of antibodies against A2 fusion protein in kala-azar immune serum by immunoprecipitation.

To produce the A2 protein in a heterologous system, the coding region from the initiating ATG to the Xba I restriction site (see FIG. 8) was subcloned in the pET 16B expression vector in frame with the HIS-TAG (FIG. 10). The A2 fusion protein of 27 kD was produced in an in Vitro transcription-translation assay (TNT system, Promega) using the pET16b/ORF II plasmid and a negative control pBluescript/p53 plasmid, encoding the human p53 protein. The in vitro translated HIS-TAG/A2 $^{35}S$-labelled protein was immunoprecipitated with kala-azar immune serum and analyzed by sodium dodecyl sulfate-polyacrylamide gel electrophoresis (FIG. 11). Kala-azar is a term used to describe the disease caused by *L. donovani.* The kala-azar immune serum was obtained from a patient suffering from visceral leishmaniasis and reacted strongly against *L. donovani* antigens on ELISA. In FIG. 11, Lanes 1 and 2 contained the labelled proteins A2 and p53, respectively, prior to immunoprecipitation analysis. Lanes 3 and 4 contained proteins A2 and p53, respectively, immunoprecipitated with the kala-azar immune serum (L1) and Lanes 5 and 6 contained proteins A2 and p53, respectively, immunoprecipitated with a control human serum (TXC). The kala-azar serum did not react against the negative control protein human p53 but did immunoprecipitate the A2 gene-product. Neither of the proteins were immunoprecipitated by the control human serum. This analysis showed that the product of the *L. donovani* A2 gene was specifically recognized by kala-azar immune serum.

Figure 12:
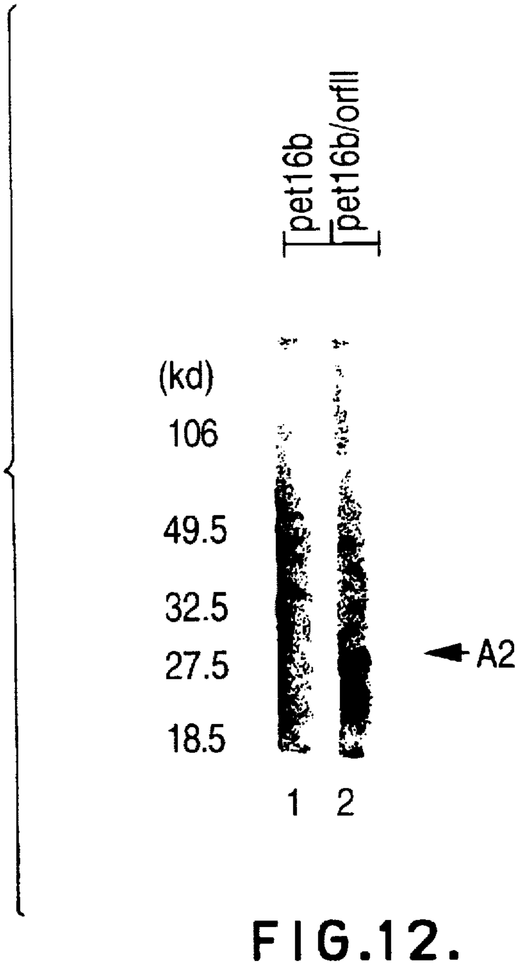
FIG. 12 shows the specific recognition of A2 fusion protein by kala-azar sera by Western blot analysis.
Figure 13:
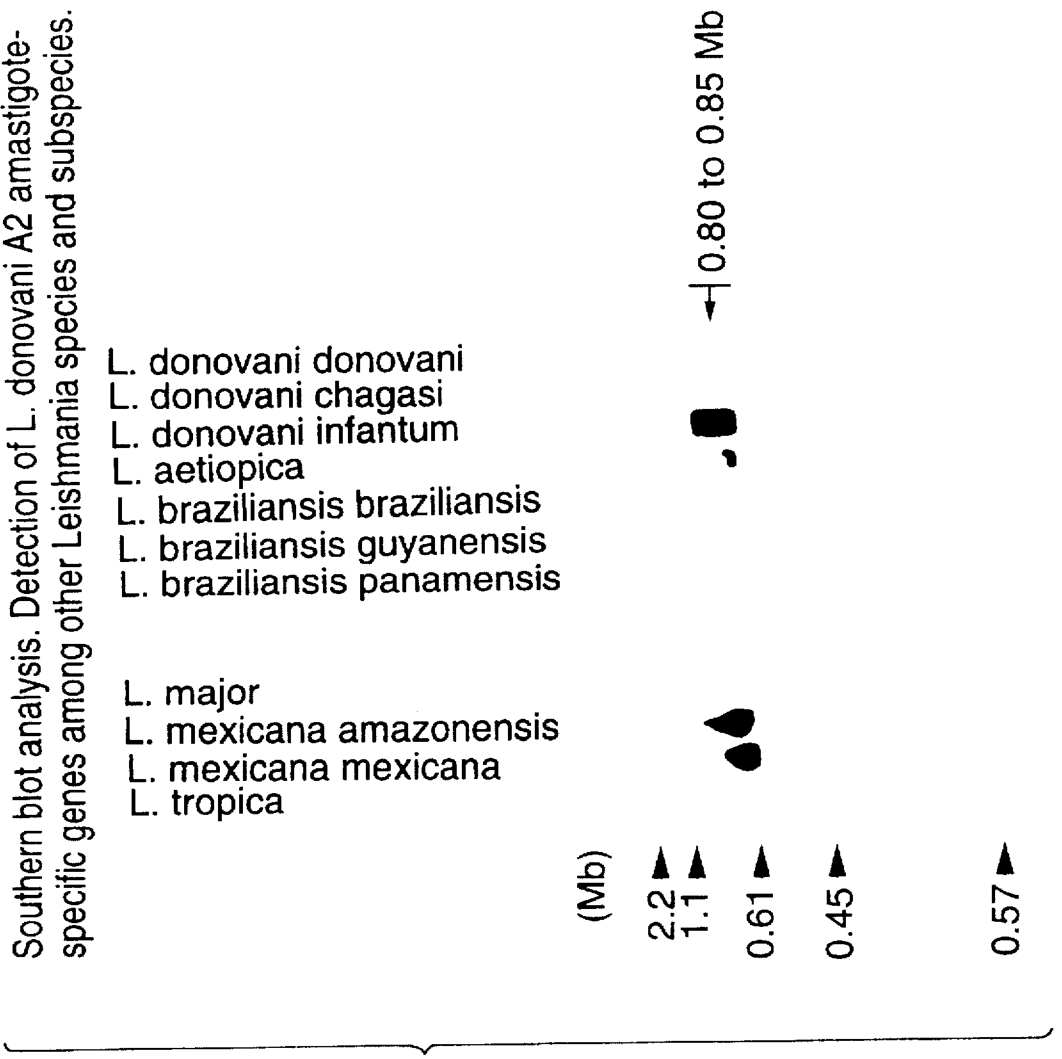

To confirm the specificity of the immune reaction, the pET 16b/ORF II plasmid coding for the recombinant A2 fusion protein and a negative control plasmid pET 16b with no insert, were introduced into *E. coli.* Expression was induced with IPTG, and total lysates of the recombinant *E. coli* cells separated by SDS-PAGE and analyzed by Western blot analysis using the kala-azar immune serum described above (see FIG. 12). In FIG. 12, Lane 1 contained *E. coli*/pET 16b cells and Lane 2 contained *E. coli*/pET 16b/ORF II cells. The kala-azar serum reacted specifically with protein products of 27.5 and 25 kD in the lysates of cells containing the pET 16b/ORF II plasmid (Lane 2). The 25 kD protein probably corresponded to the A2 protein without the HIS-TAG since the A2 sequence did contain its own initiating ATG. The serum did not react specifically with protein from *E. coli* lysates containing the control pET 16b plasmid (Lane 1). These data confirmed that the ORF II of the A2 gene encoded a *L. donovani* protein (A2) that was antigenic in patients with visceral leishmaniasis.

SUMMARY OF THE DISCLOSURE

In summary of this disclosure, the present invention provides differentially expressed genes and proteins of Leishmania, including the A2 gene expressed at significantly higher levels in the amastigote stage of the life cycle when the Leishmania organism is present in macrophages than in the promastigote stage. Modifications are possible within the scope of this invention.

REFERENCES

1. WHO, Tropical Disease Report, 1989. pp 85–92.
2. Turco, S. J., and Descoteaux, A. 1992. The Lipophosphoglycan of Leishmania parasites. Annu. Rev. Microbiol. 46:65–94.
3. Sacks, D. L. 1989. Metacyclogenesis in Leishmania promastigotes. Exp. Parasitology. 69:100–103.
4. Sacks D. L., and da Silva, R. P. 1987. The generation of infective stage *L. major* promastigotes is associated with the cell-surface expression and release of a developmentally regulated glycolipid. J. Immunol. 139:3099–3106.
5. Sacks, D. L., Brodin T. N., Turco, S. J. 1990. Developmental modification of the lipophosphoglycan from *L. Major* promastigotes during metacyclogenesis. Mol. Biochemical Parasitol. 42:225–234.
6. Medina-Acosta, E., Karess, R. E., Schwartz H., and Russell, D. G. 1989. The promastigote surface protease (gp63) of Leishmania is expressed but differentially processed and localized in the amastigote stage. Mol. Biochemical Parasitol. 37:263–274.
7. Turco, S. J. and Sacks, D. L. 1991. Expression of stage-specific lipophosphoglycan in *Leishmania major* amastigotes. Mol. Biochemical Parasitol. 45:91–100.
8. McConville, M. J., and Blackwell J. M. 1991. Developmental changes in the glycosylated phosphatidylinositols of *L. donovani* J. Biol. Chem. 260:15170–5179.
9. Bogdan, C., Röllinghoff M., and Solbach, W. 1990. Evasion strategies of Leishmania parasites. Parasitol. Today. 6:183–187.
10. Modabber, F. 1989. Experiences with vaccines against cutaneous leishmaniasis: of men and mice. Parasitol. 98:S49–S60.
11. Joshi, M., Dwyer, D. M., and Nakhasi, H. L. 1993. Cloning and characterization of differentially expressed genes from in vitro-grown "amastigotes" of *Leishmania donovani.* Mol. Biochemical Parasitol. 58:345–354.

12. Descoteaux, A., and Matlashewski, G. 1989. c-fos and tumor necrosis factor gene expression in *Leishmania donovani*-infected macrophages. Mol. Cell. Biol. 9:5223–5227.

13. Doyle, P. S. Engel, J. C., Pimenta, P. F. P. da Silva, P. and Dwyer. 1991. *Leishmania donovani:* Long-term culture of axenic amastigotes at 37° C. Exp. Parasitol. 73:326–334.

14. Sambrook, J., Fritsch, E. F., and Maniatis. 1989. Molecular cloning. A laboratory guide. Cold Spring Harbor Laboratories Press, New York. pp 7.26–7.29.

15. Sambrook, J., Fritsch, E. F., and Maniatis. 1989. Molecular cloning. A laboratory guide. Cold Spring Harbor Laboratories Press, New York. pp 10.44–10.45.

16. Sambrook, J., Fritsch, E. F., and Maniatis. 1989. Molecular cloning. A laboratory guide. Cold Spring Harbor Laboratories Press, New York. pp 9.38–9.40.

17. Sambrook, J., Fritsch, E. F., and Maniatis. 1989. Molecular cloning. A laboratory guide. Cold Spring Harbor Laboratories Press, New York. pp 4.48.

18. Cruz, A., and Beverley, S. M. 1990. Gene-replacement in parasitic protozoa. Nature 348:171–173.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1091 base pairs
( B ) TYPE: nucleic acid
( C ) STRANDEDNESS: single
( D ) TOPOLOGY: linear ( x i ) SEQUENCE DESCRIPTION: SEQ ID NO:1:

```
GAGCTCCCCC AGCGACCCTC TCGGCAACGC GAGCGCCCCA GTCCCCCCAC GCACAACTTT      60
GACCGAGCAC AATGAAGATC CGCAGCGTGC GTCCGCTTGT GGTGTTGCTG GTGTGCGTCG     120
CGGCGGTGCT CGCACTCAGC GCCTCCGCTG AGCCGCACAA GGCGGCCGTT GACGTCGGCC     180
CGCTCTCCGT TGGCCCGCAG TCCGTCGGCC CGCTCTCTGT TGGCCCGCAG GCTGTTGGCC     240
CGCTCTCCGT TGGCCCGCAG TCCGTCGGCC CGCTCTCTGT TGGCCCGCAG GCTGTTGGCC     300
CGCTCTCTGT TGGCCCGCAG TCCGTTGGCC CGCTCTCCGT TGGCCCGCTC TCCGTTGGCC     360
CGCAGTCTGT TGGCCCGCTC TCCGTTGGCT CGCAGTCCGT CGGCCCGCTC TCTGTTGGTC     420
CGCAGTCCGT CGGCCCGCTC TCCGTTGGCC CGCAGGCTGT TGGCCCGCTC TCCGTTGGCC     480
CGCAGTCCGT CGGCCCGCTC TCTGTTGGCC CGCAGGCTGT TGGCCCGCTC TCTGTTGGCC     540
CGCAGTCCGT TGGCCCGCTC TCCGTTGGCC CGCAGTCTGT TGGCCCGCTC TCCGTTGGCT     600
CGCAGTCCGT CGGCCCGCTC TCTGTTGGTC CGCAGTCCGT CGGCCCGCTC TCCGTTGGCC     660
CGCAGTCTGT CGGCCCGCTC TCCGTTGGCC CGCAGTCCGT CGGCCCGCTC TCCGTTGGTC     720
CGCAGTCCGT TGGCCCGCTC TCCGTTGGCC CGCAGTCCGT TGACGTTTCT CCGGTGTCTT     780
AAGGCTCGGC GTCCGCTTTC CGGTGTGCGT AAAGTATATG CCATGAGGCA TGGTGACGAG     840
GCAAACCTTG TCAGCAATGT GGCATTATCG TACCCGTGCA AGAGCAACAG CAGAGCTGAG     900
TGTTCAGGTG GCCACAGCAC CACGCTCCTG TGACACTCCG TGGGGTGTGT GTGACCTTGG     960
CTGCTGTTGC CAGGCGGATG AACTGCGAGG GCCACAGCAG CGCAAGTGCC GCTTCCAACC    1020
TTGCGACTTT CACGCCACAG ACGCATAGCA GCGCCCTGCC TGTCGCGGCG CATGCGGGCA    1080
AGCCATCTAG A                                                         1091
```

( 2 ) INFORMATION FOR SEQ ID NO:2:

( i ) SEQUENCE CHARACTERISTICS:
( A ) LENGTH: 711 base pairs
( B ) TYPE: nucleic acid
( C ) STRANDEDNESS: single
( D ) TOPOLOGY: linear -continued ( x i ) SEQUENCE DESCRIPTION: SEQ ID NO:2:

```
ATGAAGATCC GCAGCGTGCG TCCGCTTGTG GTGTTGCTGG TGTGCGTCGC GGCGGTGCTC    60
GCACTCAGCG CCTCCGCTGA GCCGCACAAG GCGGCCGTTG ACGTCGGCCC GCTCTCCGTT   120
GGCCCGCAGT CCGTCGGCCC GCTCTCTGTT GGCCCGCAGG CTGTTGGCCC GCTCTCCGTT   180
GGCCCGCAGT CCGTCGGCCC GCTCTCTGTT GGCCCGCAGG CTGTTGGCCC GCTCTCTGTT   240
GGCCCGCAGT CCGTTGGCCC GCTCTCCGTT GGCCCGCTCT CCGTTGGCCC GCAGTCTGTT   300
GGCCCGCTCT CCGTTGGCTC GCAGTCCGTC GGCCCGCTCT CTGTTGGTCC GCAGTCCGTC   360
GGCCCGCTCT CCGTTGGCCC GCAGGCTGTT GGCCCGCTCT CCGTTGGCCC GCAGTCCGTC   420
GGCCCGCTCT CTGTTGGCCC GCAGGCTGTT GGCCCGCTCT CTGTTGGCCC GCAGTCCGTT   480
GGCCCGCTCT CCGTTGGCCC GCAGTCTGTT GGCCCGCTCT CCGTTGGCTC GCAGTCCGTC   540
GGCCCGCTCT CTGTTGGTCC GCAGTCCGTC GGCCCGCTCT CCGTTGGCCC GCAGTCTGTC   600
GGCCCGCTCT CCGTTGGCCC GCAGTCCGTC GGCCCGCTCT CCGTTGGTCC GCAGTCCGTT   660
GGCCCGCTCT CCGTTGGCCC GCAGTCCGTT GACGTTTCTC CGGTGTCTTA A            711
```

( 2 ) INFORMATION FOR SEQ ID NO:3:

( i ) SEQUENCE CHARACTERISTICS:
( A ) LENGTH: 236 amino acids
( B ) TYPE: amino acid
( C ) STRANDEDNESS: single
( D ) TOPOLOGY: linear ( x i ) SEQUENCE DESCRIPTION: SEQ ID NO:3:

```
Met Lys Ile Arg Ser Val Arg Pro Leu Val Val Leu Leu Val Cys Val
1               5                   10                  15

Ala Ala Val Leu Ala Leu Ser Ala Ser Ala Glu Pro His Lys Ala Ala
            20                  25                  30

Val Asp Val Gly Pro Leu Ser Val Gly Pro Gln Ser Val Gly Pro Leu
        35                  40                  45

Ser Val Gly Pro Gln Ala Val Gly Pro Leu Ser Val Gly Pro Gln Ser
    50                  55                  60

Val Gly Pro Leu Ser Val Gly Pro Gln Ala Val Gly Pro Leu Ser Val
65                  70                  75                  80

Gly Pro Gln Ser Val Gly Pro Leu Ser Val Gly Pro Leu Ser Val Gly
                85                  90                  95

Pro Gln Ser Val Gly Pro Leu Ser Val Gly Ser Gln Ser Val Gly Pro
            100                 105                 110

Leu Ser Val Gly Pro Gln Ser Val Gly Pro Leu Ser Val Gly Pro Gln
        115                 120                 125

Ala Val Gly Pro Leu Ser Val Gly Pro Gln Ser Val Gly Pro Leu Ser
    130                 135                 140

Val Gly Pro Gln Ala Val Gly Pro Leu Ser Val Gly Pro Gln Ser Val
145                 150                 155                 160

Gly Pro Leu Ser Val Gly Pro Gln Ser Val Gly Pro Leu Ser Val Gly
                165                 170                 175

Ser Gln Ser Val Gly Pro Leu Ser Val Gly Pro Gln Ser Val Gly Pro
            180                 185                 190

Leu Ser Val Gly Pro Gln Ser Val Gly Pro Leu Ser Val Gly Pro Gln
        195                 200                 205

Ser Val Gly Pro Leu Ser Val Gly Pro Gln Ser Val Gly Pro Leu Ser
    210                 215                 220

Val Gly Pro Gln Ser Val Asp Val Ser Pro Val Ser
```

-continued

```
225                             230                             235
```

( 2 ) INFORMATION FOR SEQ ID NO:4:

( i ) SEQUENCE CHARACTERISTICS:
( A ) LENGTH: 269 amino acids
( B ) TYPE: amino acid
( C ) STRANDEDNESS: single
( D ) TOPOLOGY: linear ( x i ) SEQUENCE DESCRIPTION: SEQ ID NO:4:

```
Pro Gly Ser Glu Gly Pro Lys Gly Thr Gly Gly Pro Gly Ser Glu Gly
1               5                   10                  15

Pro Lys Gly Thr Gly Gly Pro Gly Ser Glu Gly Pro Lys Gly Thr Gly
            20                  25                  30

Gly Pro Gly Ser Glu Gly Pro Lys Gly Thr Gly Gly Pro Gly Ser Glu
        35                  40                  45

Gly Pro Lys Gly Thr Gly Gly Pro Gly Ser Glu Gly Pro Lys Gly Thr
    50                  55                  60

Gly Gly Pro Gly Ser Glu Gly Pro Lys Gly Thr Gly Gly Pro Gly Ser
65                  70                  75                  80

Glu Gly Pro Lys Gly Thr Gly Gly Pro Gly Ser Glu Gly Pro Lys Gly
                85                  90                  95

Thr Gly Gly Pro Gly Ser Glu Gly Pro Lys Gly Thr Gly Gly Pro Gly
            100                 105                 110

Ser Glu Gly Pro Lys Gly Thr Gly Gly Pro Gly Ser Glu Gly Pro Lys
        115                 120                 125

Gly Thr Gly Gly Pro Gly Ser Glu Gly Pro Lys Gly Thr Gly Gly Pro
    130                 135                 140

Gly Ser Glu Gly Pro Lys Gly Thr Gly Gly Pro Gly Ser Glu Gly Pro
145                 150                 155                 160

Lys Gly Thr Gly Gly Pro Gly Ser Glu Gly Pro Lys Gly Thr Gly Gly
                165                 170                 175

Pro Gly Ser Glu Ser Pro Lys Gly Thr Gly Gly Pro Gly Ser Glu Gly
            180                 185                 190

Pro Lys Gly Thr Gly Gly Pro Gly Ser Glu Gly Pro Lys Gly Thr Gly
        195                 200                 205

Pro Lys Gly Thr Gly Gly Pro Gly Ser Glu Ala Gly Thr Glu Gly Pro
    210                 215                 220

Lys Gly Thr Gly Gly Pro Gly Ser Glu Ala Gly Thr Glu Gly Pro Lys
225                 230                 235                 240

Gly Thr Gly Gly Pro Gly Ser Gly Gly Glu His Ser His Asn Lys Lys
                245                 250                 255

Lys Ser Lys Lys Ser Ile Met Asn Met Leu Ile Gly Val
            260                 265
```

What we claim is:

1. An isolated and purified DNA fragment having the nucleotide sequence:

```
GAGCTCCCCC AGCGACCCTC TCGGCAACGC GAGCGCCCCA GTCCCCCCAC GCACAACTTT    60
GACCGAGCAC AATGAAGATC CGCAGCGTGC GTCCGCTTGT GGTGTTGCTG GTGTGCGTCG   120
CGGCGGTGCT CGCACTCAGC GCCTCCGCTG AGCCGCACAA GGCGGCCGTT GACGTCGGCC   180
CGCTCTCCGT TGGCCCGCAG TCCGTCGGCC CGCTCTCTGT TGGCCCGCAG GCTGTTGGCC   240
CGCTCTCCGT TGGCCCGCAG TCCGTCGGCC CGCTCTCTGT TGGCCCGCAG GCTGTTGGCC   300
CGCTCTCTGT TGGCCCGCAG TCCGTTGGCC CGCTCTCCGT TGGCCCGCTC GCCGTTGGCC   360
CGCAGTCTGT TGGCCCGCTC TCCGTTGGCT CGCAGTCCGT CGGCCCGCTC GCTGTTGGTC   420
```

-continued

```
CGCAGTCCGT CGGCCCGCTC TCCGTTGGCC CGCAGGCTGT TGGCCCGCTC TCCGTTGGCC    480
CGCAGTCCGT CGGCCCGCTC TCTGTTGGCC CGCAGGCTGT TGGCCCGCTC TCTGTTGGCC    540
CGCAGTCCGT TGGCCCGCTC TCCGTTGGCC CGCAGTCTGT TGGCCCGCTC TCCGTTGGCT    600
CGCAGTCCGT CGGCCCGCTC TCTGTTGGTC CGCAGTCCGT CGGCCCGCTC TCCGTTGGCC    660
CGCAGTCTGT CGGCCCGCTC TCCGTTGGCC CGCAGTCCGT CGGCCCGCTC TCCGTTGGTC    720
CGCAGTCCGT TGGCCCGCTC TCCGTTGGCC CGCAGTCCGT TGACGTTTCT CCGGTGTCTT    780
AAGGCTCGGC GTCCGCTTTC CGGTGTGCGT AAAGTATATG CCATGAGGCA TGGTGACGAG    840
GCAAACCTTG TCAGCAATGT GGCATTATCG TACCCGTGCA AGAGCAACAG CAGAGCTGAG    900
TGTTCAGGTG GCCACAGCAC CACGCTCCTG TGACACTCCG TGGGGTGTGT GTGACCTTGG    960
CTGCTGTTGC CAGGCGGATG AACTGCGAGG GCCACAGCAG CGCAAGTGCC GCTTCCAACC   1020
TTGCGACTTT CACGCCACAG ACGCATAGCA GCGCCCTGCC TGTCGCGGCG CATGCGGGCA   1080
AGCCATCTAG A                                                        1091
```

(SEQ ID NO: 1), or its complementary strand.

2. An isolated and purified DNA fragment having the nucleotide sequence:

```
ATGAAGATCC GCAGCGTGCG TCCGCTTGTG GTGTTGCTGG TGTGCGTCGC GGCGGTGCTC     60
GCACTCAGCG CCTCCGCTGA GCCGCACAAG GCGGCCGTTG ACGTCGGCCC GCTCTCCGTT    120
GGCCCGCAGT CCGTCGGCCC GCTCTCTGTT GGCCCGCAGG CTGTTGGCCC GCTCTCCGTT    180
GGCCCGCAGT CCGTCGGCCC GCTCTCTGTT GGCCCGCAGG CTGTTGGCCC GCTCTCTGTT    240
GGCCCGCAGT CCGTTGGCCC GCTCTCCGTT GGCCCGCTCT CCGTTGGCCC GCAGTCTGTT    300
GGCCCGCTCT CCGTTGGCTC GCAGTCCGTC GGCCCGCTCT CTGTTGGTCC GCAGTCCGTC    360
GGCCCGCTCT CCGTTGGCCC GCAGGCTGTT GGCCCGCTCT CCGTTGGCCC GCAGTCCGTC    420
GGCCCGCTCT CTGTTGGCCC GCAGGCTGTT GGCCCGCTCT CTGTTGGCCC GCAGTCCGTT    480
GGCCCGCTCT CCGTTGGCCC GCAGTCTGTT GGCCCGCTCT CCGTTGGCTC GCAGTCCGTC    540
GGCCCGCTCT CTGTTGGTCC GCAGTCCGTC GGCCCGCTCT CCGTTGGCCC GCAGTCTGTC    600
GGCCCGCTCT CCGTTGGCCC GCAGTCCGTC GGCCCGCTCT CCGTTGGTCC GCAGTCCGTT    660
GGCCCGCTCT CCGTTGGCCC GCAGTCCGTT GACGTTTCTC CGGTGTCTTA A            711
```

(SEQ ID NO: 2), or its complementary strand.

3. An isolated and purified DNA fragment encoding the amino acid sequence:

```
Met Lys Ile Arg Ser Val Arg Pro Leu Val Val Leu Leu Val Cys Val
1               5                   10                  15

Ala Ala Val Leu Ala Leu Ser Ala Ser Ala Glu Pro His Lys Ala Ala
            20                  25                  30

Val Asp Val Gly Pro Leu Ser Val Gly Pro Gln Ser Val Gly Pro Leu
        35                  40                  45

Ser Val Gly Pro Gln Ala Val Gly Pro Leu Ser Val Gly Pro Gln Ser
    50                  55                  60

Val Gly Pro Leu Ser Val Gly Pro Gln Ala Val Gly Pro Leu Ser Val
65                  70                  75                  80

Gly Pro Gln Ser Val Gly Pro Leu Ser Val Gly Pro Leu Ser Val Gly
                85                  90                  95

Pro Gln Ser Val Gly Pro Leu Ser Val Gly Ser Gln Ser Val Gly Pro
            100                 105                 110

Leu Ser Val Gly Pro Gln Ser Val Gly Pro Leu Ser Val Gly Pro Gln
        115                 120                 125

Ala Val Gly Pro Leu Ser Val Gly Pro Gln Ser Val Gly Pro Leu Ser
    130                 135                 140

Val Gly Pro Gln Ala Val Gly Pro Leu Ser Val Gly Pro Gln Ser Val
145                 150                 155                 160

Gly Pro Leu Ser Val Gly Pro Gln Ser Val Gly Pro Leu Ser Val Gly
                165                 170                 175

Ser Gln Ser Val Gly Pro Leu Ser Val Gly Pro Gln Ser Val Gly Pro
            180                 185                 190

Leu Ser Val Gly Pro Gln Ser Val Gly Pro Leu Ser Val Gly Pro Gln
        195                 200                 205

Ser Val Gly Pro Leu Ser Val Gly Pro Gln Ser Val Gly Pro Leu Ser
    210                 215                 220

Val Gly Pro Gln Ser Val Asp Val Ser Pro Val Ser
225                 230                 235
```

(SEQ ID NO: 3), or its complementary strand.

4. A recombinant plasmid adapted for transformation of a microbial host, the recombinant plasmid comprising a plasmid vector into which a DNA segment comprising the isolated and purified DNA molecule of claim 1, 2, or 2 has been inserted.

5. The recombinant plasmid of claim 4 which is plasmid pGECO 90 having ATCC accession number 75510.

* * * * *

UNITED STATES PATENT AND TRADEMARK OFFICE

CERTIFICATE OF CORRECTION

PATENT NO. : 5,733,778

DATED : March 31, 1998

INVENTOR(S) : Matlashewski et al.

It is certified that error appears in the above-identified patent and that said Letters Patent is hereby corrected as shown below:

Title page, item [73], Assignee: McGill University Montreal, Canada

Signed and Sealed this

First Day of May, 2001

Attest:

Nicholas P. Godici

NICHOLAS P. GODICI

*Attesting Officer* *Acting Director of the United States Patent and Trademark Office*